(12) United States Patent
Sobotta et al.

(10) Patent No.: US 6,476,225 B2
(45) Date of Patent: Nov. 5, 2002

(54) PROCESS FOR PURIFYING 20(S)-CAMPTOTHECIN

(75) Inventors: Rainer Sobotta, Ingelheim (DE); Armin Rapp, Bingen-Dromersheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/051,707

(22) Filed: Jan. 17, 2002

(65) Prior Publication Data

US 2002/0111489 A1 Aug. 15, 2002

Related U.S. Application Data

(60) Provisional application No. 60/274,354, filed on Mar. 8, 2001.

(30) Foreign Application Priority Data

Feb. 15, 2001 (DE) .......................................... 101 06 969

(51) Int. Cl.$^7$ ...................... C07D 49/22; A61K 31/4738
(52) U.S. Cl. ......................................... 546/48; 514/283
(58) Field of Search ....................... 546/48, 51; 514/283

(56) References Cited

FOREIGN PATENT DOCUMENTS

WO 94/19353 * 9/1994 .................. 546/48

* cited by examiner

*Primary Examiner*—Charanjit S. Aulakh
(74) *Attorney, Agent, or Firm*—Robert P. Raymond; Timothy X. Witkowski; Mary-Ellen Devlin

(57) ABSTRACT

A process for purifying 20(S)-camptothecin, the process comprising:

(a) combining an aqueous base and a starting material containing 20(S)-camptothecin to convert the lactone ring of the 20(S)-camptothecin into a carboxylate salt;

(b) hydrogenating to the product of step (a) in the presence of a transition metal catalyst;

(c) acidifying the aqueous phase of the product of step (b) to form 20(S)-camptothecin crystals;

(d) adding at least one polar aprotic solvent to the product of step (c); and (e) separating off the purified 20(S)-camptothecin crystals.

20 Claims, No Drawings

PROCESS FOR PURIFYING 20(S)-CAMPTOTHECIN

RELATED APPLICATIONS

Benefit under 35 U.S.C. §119(e) of prior provisional application Serial No. 60/274,354, filed Mar. 8, 2001, is hereby claimed.

FIELD OF THE INVENTION

The invention relates to a process for purifying 20(S)-camptothecin contaminated by a vinyl-camptothecin derivative.

BACKGROUND OF THE INVENTION

20(S)-camptothecin (20(S)-CPT) is a natural alkaloid of formula (I)

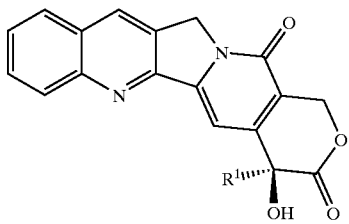

wherein $R^1$ denotes ethyl.

20(S)-CPT and its derivatives, being topoisomerase I inhibitors, have tumour-inhibiting properties (e.g., B. C. Giovanelle et al., Cancer Research, 51: 302–3055, 1991; European Patent Applications EP 0 074 256 and EP 0 088 642; U.S. Pat. Nos. 4,473,692, 4,545,880, and 4,604,463; and International Patent Application WO 92/05785).

20(S)-CPT can be obtained as a crude product from the Chinese tree *Camptotheca acuminata* (Nyssaceae) (M. Wall et al., J. Am. Chem. Soc. 88: 3888–3890, 1966) or from the Indian tree *Nothapodytes foetida* (*nimmoniana*) (formerly known as: *Mappie foetida Miers*) (T. R. Govindachari et al., Phytochemistry 11: 3529–3531, 1972), inter alia.

These crude products, particularly the one obtained from *Nothapodytes foetida*, contain 20(S)-CPT contaminated by a CPT derivative of formula (I) wherein $R^1$ denotes vinyl (20-vinyl-CPT).

Traditionally, the crude products are purified by complex chromatographic methods or by converting the camptothecin into the aqueous phase and eliminating impurities by extraction with water-insoluble solvents (e.g., WO 94/19353). However, contamination by 20-vinyl-CPT cannot be efficiently dealt with by these methods.

The problem of the present invention is therefore to provide a process which allows the 20(S)-CPT starting product to be purified without using complex chromatographic methods.

DESCRIPTION OF THE INVENTION

Surprisingly, it has been found that 20(S)-CPT can be virtually completely freed from contamination with 20-vinyl-CPT by first treating the starting material with an aqueous base, hydrogenating and subsequently acidifying it and then isolating the product.

The invention thus relates to a process for purifying 20(S)-camptothecin which comprises the following steps:
(a) combining an aqueous base and a starting material containing 20(S)-camptothecin, thereby converting the lactone ring of the 20(S)-camptothecin into a carboxylate salt;
(b) hydrogenating the resulting mixture in the presence of a transition metal catalyst;
(c) acidifying the aqueous phase, thereby forming camptothecin crystals;
(d) adding a polar aprotic solvent; and
(e) separating off the camptothecin crystals.

The invention further relates to a process for preparing 20(S)-camptothecin of formula (I) wherein $R^1$ denotes ethyl, from 20-vinyl-camptothecine of formula (I) wherein $R^1$ denotes vinyl, which comprises the following steps:
(a) combining an aqueous base and the starting material containing 20(S)-camptothecin, forming a compound of formula (II),

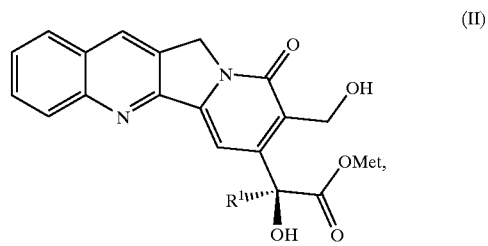

wherein: $R^1$ denotes vinyl, and Met denotes a metal;
(b) hydrogenating the resulting mixture in the presence of a transition metal catalyst;
(c) acidifying the aqueous phase to form camptothecin crystals;
(d) adding at least one polar aprotic solvent; and
(e) separating off the camptothecin crystals.

DETAILED DESCRIPTION OF THE INVENTION

The term "starting material containing camptothecin" as used above and hereinafter refers to a contaminated material containing 20(S)-CPT, crude camptothecin, camptothecin-containing plant extracts, synthetic camptothecin, derivatives of camptothecin as described, for example, in International Patent Application WO 92/05785, or reaction products containing camptothecin.

Preferably, the starting material is a natural crude product which is obtained in particular from *Nothapodytes foetida*. As a rule, it is a mixture of the compound of formula (I) wherein $R^1$ denotes ethyl, and the compound of formula (I) wherein $R^1$ denotes vinyl. It generally contains 0.9 wt. % to 1.5 wt. %, preferably 1.0 wt. % to 1.4 wt. % of the vinyl compound. In addition, the starting material may contain other camptothecin derivatives such as, for example, 9-methoxy-CPT, 10-methoxy-CPT, 11-methoxy-CPT, 10-hydroxy-CPT, and 11-hydroxy-CPT. As a rule, the starting material contains up to 1 wt. % of one or more of these additional CPT derivatives, particularly 0.2 wt. % to 0.8 wt. % of 9-methoxy-CPT.

The term "aqueous base" as used above and hereinafter in connection with step (a) of the purification process according to the invention relates to a base which generates enough hydroxide ions in the aqueous medium, preferably in pure water, to convert the lactone group of the camptothecin derivatives contained in the starting material completely into the corresponding hydroxycarboxylates. Metal hydroxides are preferred, particularly alkali metal or alkaline earth metal hydroxides such as lithium hydroxide, sodium hydroxide, potassium hydroxide or calcium hydroxide. Sodium hydroxide is most preferred.

The metal hydroxide is preferably used in the form of a dilute aqueous solution, preferably in the form of a 1% to 25%, particularly a 3% to 10% aqueous solution. As a rule, sufficient metal hydroxide is used to make the camptothecin derivatives go completely into solution; preferably, 1 mol to 20 mol, more preferably 5 mol to 15 mol, particularly 7.5 mol to 12.5 mol of metal hydroxide are used per 1 mol of starting material.

In step (b) a transition metal catalyst, preferably a heterogeneous transition metal catalyst, particularly platinum, platinum oxide, nickel, palladium or rhodium on a carrier material such as activated charcoal or aluminium oxide is added to the resulting mixture. Palladium on activated charcoal containing 1 wt. % to 15 wt. %, preferably 2 wt. % to 10 wt. %, particularly about 5 wt. % of palladium is particularly preferred.

The quantity of transition metal catalyst is selected so as to ensure total hydrogenation of the vinylic CPT derivative. Preferably, 0.01 to 0.50 parts by weight, particularly 0.02 to 0.10 parts by weight of transition metal catalyst (including carrier materials) are used, based on 1 part by weight of the starting material.

The resulting mixture is subjected to the action of hydrogen gas, preferably at a temperature of −20° C. to 100° C., particularly 10° C. to 40° C., most preferably at about room temperature.

The hydrogen pressure is not critical per se; the hydrogenation is preferably carried out at normal pressure or at slightly raised pressure, particularly at 0.9 bar to 5.0 bar, most preferably at about 1 bar.

Under these conditions, hydrogenation is generally complete within 1 to 20 hours, preferably 4 to 15 hours, particularly 6 to 10 hours.

After the hydrogenation has ended, the transition metal catalyst is preferably eliminated by filtration, and the resulting reaction mixture is acidified in step (c). The acidification can be done with an inorganic or organic acid. Preferred acids are inorganic acids such as HCl, HBr, HI, $HNO_3$, $H_3PO_4$, $H_2SO_4$, or aliphatic carboxylic acids such as acetic acid and trifluoroacetic acid or mixtures of these acids, particularly concentrated hydrochloric acid. Using the chosen acid, the pH is adjusted to 3.0 to 6.0, preferably 3.5 to 5.0, particularly about 4.0 to 4.5. The reaction with the acid is generally carried out at a temperature of 0° C. to 100° C., preferably 30° C. to 80° C., particularly 50° C. to 60° C.

In a particularly preferred embodiment, acidification is carried out with 2 to 20 parts by weight, preferably 4 to 9 parts by weight, particularly 6 to 8 parts by weight of concentrated hydrochloric acid, based on 1 part by weight of starting material.

Under the conditions described, lactonization to form the CPT is generally complete within 10 to 180 minutes, preferably 15 to 60 hours, particularly within about 30 minutes.

The reaction mixture obtained by acidification is generally in the form of a pure suspension. To improve the crystallization in step (d) one or more polar aprotic solvents are added thereto. Suitable solvents of this kind are preferably sulfoxides such as dimethylsulfoxide (DMSO) or amides and urea derivatives of formula

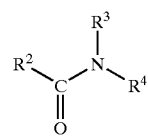

wherein
  $R^2$ denotes hydrogen or a $C_{1-4}$ alkyl group, particularly hydrogen or methyl;
  $R^3$ and $R^4$ independently of each other denote a $C_{1-4}$ alkyl group, particularly methyl; or
  $R^2$ and $R^3$ together denote a —$(CH_2)_m$— or a —$NR^5$—$(CH_2)_n$— group, while
  $R^5$ denotes a $C_{1-4}$ alkyl group;
  m is 3 or 4, particularly 3; and
  n is 2 or 3,
particularly selected from among N,N-dimethylformamide (DMF), N,N-dimethylacetamide (DMA), N-methylpyrrolidone (NMP), N,N-dimethylethylene urea (DMEU), and N,N-dimethylpropylene urea (DMPU) or mixtures of these solvents, most preferably DMF.

As a rule, 10 to 100 parts by weight, preferably 20 to 80 parts by weight, particularly 30 to 50 parts by weight of the polar aprotic solvent are used, based on 1 part by weight of the starting material used.

The treatment with the polar aprotic solvent may be carried out at any desired temperature. The reaction mixture is preferably stirred at a temperature of 30° C. to 120° C., particularly 80° C. to 100° C. and then slowly cooled to ambient temperature.

The CPT crystals thus obtained are easily separated from the liquid phase in step (e), preferably by decanting, centrifuging, spinning, squeezing out or filtration, particularly by filtration.

As a rule, the CPT crystals thus obtained are washed with an alcohol, preferably methanol, ethanol or isopropanol, particularly methanol, and dried.

The advantage of the procedure according to the invention is the high space/time yield and the high yield and purity of the 20(S)-camptothecin produced, which is obtained without any chromatographic purification substantially free from contaminants containing vinyl groups.

The Examples that follow serve to illustrate some processes for purifying camptothecin carried out by way of example. They are intended only as possible methods given as examples, without restricting the invention to their content.

EXAMPLE 1

10.45 g of a crude product containing camptothecin, obtained from *Nothapodytes foetida,* containing 1.33% of 20-vinyl-CPT and 0.47% of 9-methoxy-CPT, is taken up in 260 mL of a 2 N sodium hydroxide solution and 0.6 g of palladium/activated charcoal (5%) is added. The mixture is treated with hydrogen for 8 hours at ambient temperature under a pressure of 1 bar. Then the reaction mixture is filtered and combined at 50° C.–60° C. with 80 mL of concentrated hydrochloric acid and adjusted to a pH of 4.0 to 4.5. The suspension formed is combined with 400 mL of DMF and stirred for 2.5 hours at 90° C.–100° C. The resulting suspension is slowly cooled to ambient temperature and filtered. The CPT crystals obtained are washed with 100 mL of methanol and dried at 55° C. in vacuo. 9.85 g (94.2% of material put in) of 20(S)-camptothecin are obtained, containing less than 0.05% of 20-vinyl-CPT and 0.11% of 9-methoxy CPT.

EXAMPLE 2

10.45 g of a crude product containing camptothecin, obtained from *Nothapodytes foetida,* containing 1.33% of 20-vinyl-CPT and 0.47% of 9-methoxy-CPT is taken up in 260 mL of a 2 N sodium hydroxide solution and 0.6 g of palladium/activated charcoal (5%) is added. The mixture is treated with hydrogen for 8 hours at ambient temperature under a pressure of 1 bar. Then the reaction mixture is filtered and combined at 50° C.–60° C. with 300 mL of a 10% sulfuric acid and adjusted to a pH of 4.0 to 4.5. The suspension formed is combined with 500 mL of DMF and stirred for 2.5 hours at 90° C.–100° C. The resulting suspension is slowly cooled to ambient temperature and filtered. The CPT crystals obtained are washed with 100 mL of methanol and dried at 55° C. in vacuo. 9.67 g (92.6% of material put in) of 20(S)-camptothecin are obtained, containing 0.09% of 9-methoxy CPT, the content of 20-vinyl-CPT being below the detection threshold.

We claim:

1. A process for purifying 20(S)-camptothecin, the process comprising:
   (a) combining an aqueous base and a starting material containing 20(S)-camptothecin to convert the lactone ring of the 20(S)-camptothecin into a carboxylate salt;
   (b) hydrogenating to the product of step (a) in the presence of a transition metal catalyst;
   (c) acidifying the aqueous phase of the product of step (b) to form 20(S)-camptothecin crystals;
   (d) adding at least one polar aprotic solvent to the product of step (c); and
   (e) separating off the purified 20(S)-camptothecin crystals.

2. The process for purifying 20(S)-camptothecin according to claim 1, wherein the starting material containing 20(S)-camptothecin is a natural plant product.

3. The process for purifying 20(S)-camptothecin according to claim 1, wherein the starting material containing 20(S)-camptothecin consists essentially of a mixture of the compounds of formula (I)

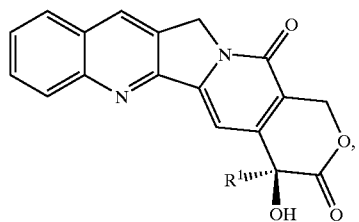

(I)

wherein $R^1$ is ethyl or vinyl.

4. The process for purifying 20(S)-camptothecin according to claim 1, wherein the base in step (a) is sodium hydroxide.

5. The process for purifying 20(S)-camptothecin according to claim 1, wherein the product of step (a) is hydrogenated in the presence of a palladium catalyst at a temperature of 0° C. to 100° C. and at a pressure of 0.5 bar to 5.0 bar.

6. The process for purifying 20(S)-camptothecin according to claim 1, wherein step (c) is performed using an acid selected from the group consisting of: HCl, HBr, HI, HNO$_3$, H$_3$PO$_4$, H$_2$SO$_4$, acetic acid, and trifluoroacetic acid, and mixtures thereof.

7. The process for purifying 20(S)-camptothecin according to claim 6, wherein step (c) occurs at a temperature of 30° C. to 80° C.

8. The process for purifying 20(S)-camptothecin according to claim 1, wherein step (d) is performed using one or more polar aprotic solvents of formula

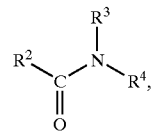

wherein:
   $R^2$ is hydrogen or a $C_{1-4}$ alkyl group; and
   $R^3$ and $R^4$ are each independently a $C_{1-4}$ alkyl group, or $R^2$ and $R^3$ together are a —(CH$_2$)$_m$— or a —NR$^5$—(CH$_2$)$_n$— group, wherein $R^5$ is a $C_{1-4}$ alkyl group, m is 3 or 4, and n is 2 or 3.

9. The process for purifying 20(S)-camptothecin according to claim 8, wherein step (c) occurs at a temperature of 30° C. to 120° C.

10. The process for purifying 20(S)-camptothecin according to claim 8, wherein the polar aprotic solvent is selected from the group consisting of: N,N-dimethylformamide (DMF), N,N-dimethylacetamide (DMA), N-methylpyrrolidone (NMP), N,N-dimethylethylene urea (DMEU), and N,N-dimethylpropylene urea (DMPU), and mixtures thereof.

11. The process for purifying 20(S)-camptothecin according to claim 1, wherein step is performed using filtration.

12. The process for purifying 20(S)-camptothecin according to claim 3, wherein the base in step (a) is sodium hydroxide.

13. The process for purifying 20(S)-camptothecin according to claim 3, wherein the product of step (a) is hydrogenated in the presence of a palladium catalyst at a temperature of 0° C. to 100° C. and at a pressure of 0.5 bar to 5.0 bar.

14. The process for purifying 20(S)-camptothecin according to claim 3, wherein step (c) is performed using an acid selected from the group consisting of: HCl, HBr, HI, HNO$_3$, H$_3$PO$_4$, H$_2$SO$_4$, acetic acid, and trifluoroacetic acid, and mixtures thereof.

15. The process for purifying 20(S)-camptothecin according to claim 14, wherein step (c) occurs at a temperature of 30° C. to 80° C.

16. The process for purifying 20(S)-camptothecin according to claim 1, wherein step (d) is performed using one or more polar aprotic solvents of formula

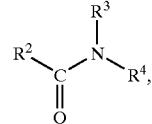

wherein:
   $R^2$ is hydrogen or a $C_{1-4}$ alkyl group; and
   $R^3$ and $R^4$ are each independently a $C_{1-4}$ alkyl group, or $R^2$ and $R^3$ together are a —(CH$_2$)$_m$— or a —NR$^5$—(CH$_2$)$_n$— group, wherein $R^5$ is a $C_{1-4}$ alkyl group, m is 3 or 4, and n is 2 or 3.

17. The process for purifying 20(S)-camptothecin according to claim 16, wherein step (c) occurs at a temperature of 30° C. to 120° C.

18. The process for purifying 20(S)-camptothecin according to claim 16, wherein the polar aprotic solvent is selected from the group consisting of: N,N-dimethylformamide (DMF), N,N-dimethylacetamide (DMA), N-methylpyrrolidone (NMP), N,N-dimethylethylene urea (DMEU), and N,N-dimethylpropylene urea (DMPU), and mixtures thereof.

19. The process for purifying 20(S)-camptothecin according to claim 3, wherein step is performed using filtration.

20. A process for preparing 20(S)-camptothecin of formula (I)

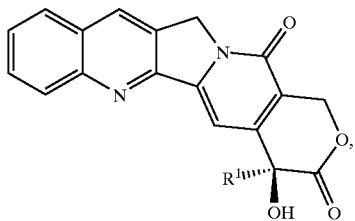

(I)

wherein $R^1$ is ethyl, from a 20-vinyl-camptothecine of formula (I) wherein $R^1$ is vinyl, the process comprising:

(a) combining an aqueous base and the starting material containing 20-vinyl-camptothecine, to form a compound of formula (II)

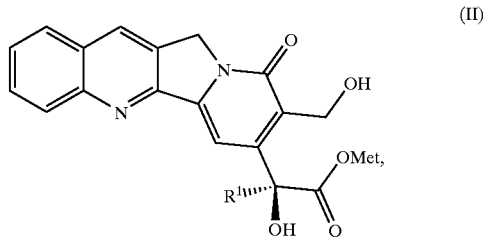

(II)

wherein $R^1$ is vinyl, and Met is a metal;

(b) hydrogenating to the product of step (a) in the presence of a transition metal catalyst;

(c) acidifying the aqueous phase of the product of step (b) to form 20(S)-camptothecin crystals;

(d) adding at least one polar aprotic solvent to the product of step (c); and (e) separating off the purified crystals of 20(S)-camptothecin of formula (I) wherein $R^1$ is ethyl.

* * * * *